United States Patent [19]
de Gracia

[11] 4,433,057
[45] Feb. 21, 1984

[54] CHEMICAL REAGENT INDICATOR FOR THE IN VITRO DIAGNOSIS OF PREGNANCY

[76] Inventor: Maria R. de Gracia, 6 Avenue Dapples, Lausanne (Vaud), Switzerland

[21] Appl. No.: 348,067

[22] PCT Filed: Jul. 3, 1980

[86] PCT No.: PCT/FR80/00109
§ 371 Date: Feb. 5, 1982
§ 102(e) Date: Feb. 5, 1982

[87] PCT Pub. No.: WO82/00060
PCT Pub. Date: Jan. 7, 1982

[30] Foreign Application Priority Data

Jun. 6, 1980 [FR] France ............... 80 12638

[51] Int. Cl.³ .................. G01N 33/52; G01N 33/76
[52] U.S. Cl. ................................................. 436/65
[58] Field of Search ........................................ 436/65

[56] References Cited

U.S. PATENT DOCUMENTS

| | | | |
|---|---|---|---|
| 3,226,196 | 12/1965 | La Vietes | 23/917 |
| 3,248,173 | 4/1966 | Stauch | 23/917 |
| 3,298,787 | 1/1967 | Fossel | 23/230 |
| 3,345,138 | 10/1967 | Eberhard et al. | 23/917 |
| 3,595,620 | 7/1971 | Gordon | 23/230 B |
| 3,813,222 | 5/1974 | La Vietes | 23/917 |

FOREIGN PATENT DOCUMENTS 2018989A of 1979 United Kingdom .

OTHER PUBLICATIONS

Chemical Abstracts, 92: 37296b (1980).
Chemical Abstracts, vol. 7, No. 2, 1971, No. 14558y.

*Primary Examiner*—Sidney Marantz
*Attorney, Agent, or Firm*—Spencer & Frank

[57] ABSTRACT

A chemical reagent for the in vitro diagnosis of pregnancy in a female mammal; said reagent to be added to a urine sample and containing
(a) a buffer solution having a pH of 5.2 to 6.6;
(b) a dye colorimetrically responsive to HCG; and
(c) a chemical component for adjusting and stabilizing the pH of the urine sample to 4–5.

16 Claims, No Drawings

CHEMICAL REAGENT INDICATOR FOR THE IN VITRO DIAGNOSIS OF PREGNANCY

The present invention relates to a chemical reagent indicator for the in vitro diagnosis of pregnancy in a female mammal, and also to the method of preparing and the method of utilizing such indicator.

It is well known to rely on the presence of human chorionic gonadotropin (H.C.G.) in the urine or serum of expectant mothers beyond the 24th day of pregnancy, with a maximum concentration between the 40th and the 60th day, for diagnosing the state of pregnancy.

Initially, biological lab tests have been carried out by using animals such as rats and rabbits.

Though the accuracy of these tests is satisfactory, the time and means necessary for accomplishing them, and consequently their cost, are rather excessive, thus making the procedure inadequate for a generalization.

Immunological tests have also been proposed which consist in determining a reaction between gonadotropin and its antibodies. These tests are also satisfactory from the point of view of precision, but suffer from the same inconveniences as biological tests: they are time-robbing, difficult to implement, and expensive.

It is therefore necessary to develop a different method which is at the same time rapid, accurate and economical, and also capable of affording an easy interpretation of the result even by the unskilled layman.

The U.S. Pat. No. 3,595,620 filed by Gordon on Oct. 28, 1968 discloses and claims a chemical reagent acting as an indicator in the in vitro diagnosis of pregnancy, by imparting a specific color to the urine when added thereto.

This reagent consists either of bromocresol purple of chlorophenol red in a buffer solution having a pH value of 6 and comprising monobasic potassium phosphate and sodium hydroxide. chlorophenol red.

The reagent is criticized on account of the small discrepancy between the color due to a negative reaction and the color due to a positive reaction, which discrepancy may drop to about one-hundred Angströms, with the possibilites of misinterpretation.

Besides, it seems that the amount of reagent implemented does not affect the result appreciably.

It is the primary object of the present invention to improve the results obtained with a Gordon-type reagent by increasing the discrepancy between the color due to a negative reaction and the color due to a positive reaction.

Besides, experience teaches that the positive test color was reinforced when the colorimetric agent utilized was a mixture of halogenated cresol (such as bromocresol purple) and halogenated chlorophenol (such as chlorophenol red), the two components producing on each other a synergetic effect controlling the degree of coloration of the positive test, the best results being obtained when the ratio of bromocresol purple to chlorophenol red was in the range of about 55% to 45% by weight, and preferably in the ratio of 53% to 47% by weight.

These tests produced a great number of wrong and dubious results in which it would have been impossible to give an affirmative answer in one or the other direction, had the sound answer not been known beforehand.

In all these cases the verifications made showed that the urines had an abnormally low pH value or an abnormally high pH value, and consequently that the urines of a non-pregnant woman (i.e. a test of which the result should normally be definitely negative) turned to the range of purple red tints, close to the range of tints which should normally correspond to the positive test.

The applicant observed that a first requirement for obtaining true results was to change the urine pH so that it ranges between 4 and 5.

Now, there is at least one case in which this acid-alkalimetry factor displays a strongly basic trend, namely when the woman has previously ingested a steroid drug, for example a contraceptive drug.

In his U.S. Pat. No. 3,595,620, Gordon, far from thinking that the presence of this type of hormone might alter the test result, had on the contrary the idea of utilizing this property for detecting the omission of taking a contraceptive pill.

It is therefore the primary object of the present invention to counteract the irregular pH by maintaining the pH at a value between 4 and 5, by adding one or more components, which are compatible with the above mentioned colorimetric agents.

The Applicant also found that among all these compatibles substances the priority should be given to (2-dimethylamino-phenyl-nitrobenzoic) methyl red and to (3-3' dibromothymol sulphonaphthalene) bromothymol blue, for these phenols themselves take an active part in the modification of the color wavelength.

The ratio by weight of methyl red to bromothymol blue is advantageously ½.

By performing such tests on the urines of non-pregnant women, the Applicant observed that the ingestion of steroid-containing compounds was not the only cause of faulty test results, since positive or dubious results were obtained unduly when the woman undergoing the test had eaten food having either a relatively high acid content (such as citric or ascorbic acid) or a relatively high protein or alcohol content.

It became apparent to the Applicant that to obtain reliable results it was necessary to prevent the reagent from interfering with the H.C.G. (human chorionic gonadotropin). It is necessary to add to the formula a compensating agent which intervenes only if necessary.

The choice proceeds on a indophenol as the dichlorophenol indophenol which has the advantage to darken the colour of the positive test then to ameliorate the reading of the result.

Considering the fact that steroids, citric acid or ascorbic acid, alcohol and proteins exert on the reagent an action similar to that exerted by the H.C.G., the Applicant inferred therefrom that the H.C.G. has a common factor with these substances and further that the common factor between these substances themselves is the presence of carbonyl groups in their composition, so that it appeared that the urines of a pregnant woman also contains these groups resulting from an in vivo reaction of the H.C.G., the latter releasing said specific groups through the human metabolism.

On the other hand, since in vitro tests bringing together the H.C.G. and the reagent of the present invention evidenced through the negative results thus obtained that though synthetic H.C.G. is an isomer mixture, natural H.C.G. is a single isomer giving selective reactions. The Applicant thought of reproducing in vitro the in vivo process by adding the following compounds: steroids, citric acid or ascorbic acid, as well as alcohol and proteins, to the urine of a non-pregnant woman. These experiments led to an altered, i.e. neither positive nor negative, result in the pregnancy test.

The conclusions deriving from these experiments show that the carbonyl groups became somehow effective in the reaction, by giving an absolute (i.e. neither negative nor positive) alteration.

The in vivo results are not identical with the in vitro results because in the in vivo experiments the compounds are subjected to the metabolic process of the human body from the time said compounds are ingested and the time they are eliminated.

Therefore, it is clear that the reaction takes place between a carbonyl group present in the urine and the reagent of the invention, said group resulting from an in vivo reaction of the H.C.G., which releases carbonyl groups specific of the metabolism of pregnant women, which groups are eliminated by the urines in which they are detected by said reagent.

The reagent should be prepared under conditions such that it cannot be disturbed by external agents, namely:

preparation in an isolated medium excluding any operation other than the preparation itself;

moisture-free and stable atmosphere;

the surrounding air temperature should not depart from the range from 20° to 25° C.;

the air must be sterile, this also applying of course to all the furniture and instruments, including the garments of the operators who must wear a similarly sterile mask;

a perfect mixing of the ingredient is necessary to avoid the presence of any residue at the end of the preparation process, otherwise the test results would be altered;

the reagent thus obtained must be preserved in dark-colored glass bottless and these bottles must be closed to complete air-tightness.

The reagent is obtained by mixing three solutions prepared separately:

Firstly, a buffer solution (Solution A) is prepared by introducing 250 milliliters of a 0.2 molar solution of sodium monobasic phosphate, to which 28 milliliters of a 0.2 molar solution of sodium hydroxide are added, into a one-liter graduated balloon flask, distilled water being subsequently added to complete the content to one liter.

Then a coloring solution (Solution B) is prepared by mixing while stirring 0.20 grams of bromocresol purple, 0.18 gr of chlorophenol red in 18 milliliters of buffer Solution A, the same solution A being then used for completing up to 700 milliliters.

Finally, Solution C is prepared by dissolving 0.10 g of methyl red and 0.20 g of bromothymol blue and 0.12 g of dichlorophenol indophenol in 250 milliliters of buffer Solution A.

The reagent is obtained by mixing Solutions B and C which are completed with distilled water up to one liter.

The reagent thus obtained is used as follows inn a pregnancy detection test:

(a) A sample of urine is taken in the morning from the fasting woman.

(b) The urine is poured into a dry, clean and hygienic container during 15 mn until the urine is at room temperature. (If the urine sample was kept in a refrigerator, it must be restored to room temperature before carrying out the experiment. In this case, the waiting time before use should not exceed the eight-hour limit. The refrigerated samples should not be kept beyond 48 days. Frozen samples can be kept as long as 25 days.).

(c) 5 centiliters of urine to which 2 drops of reagents (corresponding each to about 0.132 cc.) are added while mixing are introduced while stirring into a flat-bottomed, cylindrical, colorless container.

(d) If the mixture assumes a purple-blue, pale pink of purple-pink color, the result can be regarded as a positive one; if more than 4 drops of reagent are added, the above-mentioned colors will become more intense while remaining in the same scale.

(e) If the mixture remains in the yellow to light-brown color scale, i.e. a color in the range of the urine tested before the mixing step, and only slightly darker than the natural color of the urine used in the test, the result is negative; if more than 4 drops of reagent are added, the aforesaid color will be intensified while remaining in the same scale.

(f) The result is obtained in the matter of no more than twenty seconds.

Therefore, between the wavelength of the positive test colors and the wavelenght of the negative test colors, there is a difference of about 1,000 Å.

However, the following cares should be taken:

contraceptives should not be administered the woman less than 48 hours before carrying out the test of this invention;

during the night preceding the test, the absorption of acidifying and antiacid substances, such as oranges, lemons, meat, bicarbonate, effervescent drugs, vinegar and other similar products should be avoided;

if clorifene citrate or other fertilizing medicines have been administered during a short period or more than two weeks before the test, no interferences should appear;

to facilitate the reading and avoid any confusion between colors, the result should be observed on a white background and under natural light conditions. The reagent according to the present invention is capable of detecting the presence of H.C.G. in the urine as early as 4 to 6 days after the end of the menses.

The first experiment should be conducted between the 4th and 6th day following the end of the menses, and may be renewed during a period of three months after this date.

The best period for carrying out the test is between the fourth and seventeenth days thus calculated.

Beyond the 90th day, the hormonal rate drops considerably and entails consequently a decline in the reagent efficiency.

Finally, it should be noted that the presence of methyl red and bromothymol blue in the reagent not only produces the above-specified compensating effects in case a substance absorbed by the woman to be subjected to the test might impair the result, but imparts a nearly infinite stability to the reagent, whereas in the absence of said red and blue substances the reagent would not preserve its stability beyond two or three months.

What is claimed is:

1. A chemical reagent for the in vitro diagnosis of pregnancy, said reagent to be added to a urine sample from a female mammal, said reagent being obtained from combining the following components:

(a) a buffer solution having a pH in the range of 5.2 to 6.6;

(b) a dye colorimetrically responsive to the presence of HCG in urine; and (c) a chemical component for adjusting and stabilizing the pH of the urine sample when the chemical reagent is added thereto to a value of between 4 and 5.

2. The reagent according to claim 1, wherein the buffer solution is obtained by mixing 250 milliliters of a 0.2 molar solution of sodium monobasic phosphate, and 25 to 30 milliliters of a 0.2 molar solution of sodium hydroxide with distilled water, 15 to 20 milliliters of said buffer solution being added to 0.2 g of bromocresol purple and 0.18 g of chlorophenol red to form a coloring solution.

3. A reagent obtained by adding the coloring solution according to claim 2 is added to a mixture obtained by dissolving 0.10 g of methyl red, 0.20 g of bromothymol blue and 0.12 g of dichlorophenol indophenol in 250 milliliters of said buffer solution to form a new mixture, and completing the new mixture with distilled water up to a volume of one liter.

4. A test for the in vitro diagnosis of pregnancy, in which a colorimetric reagent is brought together with a urine sample to be tested comprising mixing one or two drops (corresponding each to about 0.132 cc) of the reagent of claim 3 with about 5 centiliters of the urine sample.

5. The reagent of claim 1, wherein said dye is a mixture of halogenated cresol and halogenated phenol.

6. Reagent according to claim 5, wherein said halogenated cresol is bromocresol purple (5'-5" dibromo-o-cresolsulphonaphthalene) and said halogenated chlorophenol is dichlorophenol red (3'-3" dichlorosulphonaphthalene).

7. Chemical reagent according to claim 6, wherein the ratio of said bromocresol purple to said dichlorophenol red is between about 55% and 45% by weight.

8. The reagent according to claim 7, wherein the ratio of said bromocresol purple to said dichlorophenol red is between about 53% and 47% by weight.

9. The reagent according to claim 1, wherein the component used for maintaining and stabilizing the pH of the tested urines between 4 and 5 is a mixture of methyl red (2 dimethyl aminophenyl) and bromothymol blue (3-3' dibromothymol sulphonaphthalene.

10. The reagent of claim 9, wherein said methyl red and bromothymol blue are in the ratio of about ½ by weight.

11. The reagent of claim 10, which comprises a solution obtained by dissolving 0.10 g of methyl red, 0.20 g of bromomethyl blue and 0.12 g of dichlorophenol indophenol in 250 milliliters of a buffer solution obtained by mixing 250 milliliters of a 0.2 molar solution of sodium monobasic phosphate and 25 to 30 milliliters of a 0.2 molar solution of sodium hydroxide with distilled water.

12. The reagent according to claim 9, wherein said dye is a mixture of halogenated cresol and halogenated phenol.

13. The reagent according to claim 12, wherein said methyl red and bromomethyl blue are in the ratio of about ½ by weight.

14. The reagent according to claim 12, wherein said halogenated cresol is bromocresol purple (5'-5" dibromo-o-cresolsulphonaphthalene) and said halogenated chlorophenol is dichlorophenol red (3'-3" dichlorosulphonaphthalene).

15. The reagent according to claim 14, wherein said methyl red and bromomethyl blue are in the ratio of about ½ by weight.

16. The reagent according to claim 14, wherein the buffer solution is obtained by mixing 250 milliliters of a 0.2 molar solution of sodium monobasic phosphate, and 25 to 30 milliliters of a 0.2 molar solution of sodium hydroxide with distilled water, 15 to 20 milliliters of said buffer solution being added to 0.2 g of bromocresol purple and 0.18 g of chlorophenol red to form a coloring solution.

* * * * *